US005947928A

United States Patent [19]
Muller

[11] Patent Number: 5,947,928
[45] Date of Patent: Sep. 7, 1999

[54] DRUG DELIVERY SYSTEM

[75] Inventor: David F. Muller, Boston, Mass.

[73] Assignee: Mile Creek Capital, LLC, Boston, Mass.

[21] Appl. No.: 08/879,156

[22] Filed: Jun. 19, 1997

[51] Int. Cl.⁶ ................................................. A61M 37/00
[52] U.S. Cl. ........................ 604/140; 604/145; 604/147; 604/131
[58] Field of Search .................... 604/131, 132, 604/133, 140, 141, 143, 145, 146, 148

[56] References Cited

U.S. PATENT DOCUMENTS

| | | | |
|---|---|---|---|
| 3,308,818 | 3/1967 | Rutkowski | 128/173 |
| 4,596,556 | 6/1986 | Morrow et al. | 604/70 |
| 4,790,824 | 12/1988 | Morrow et al. | 604/143 |
| 4,890,603 | 1/1990 | Filler | 128/24 A |
| 4,940,460 | 7/1990 | Casey, I et al. | 604/143 |
| 4,941,880 | 7/1990 | Burns | 604/143 |
| 4,945,050 | 7/1990 | Sanford et al. | 435/172.1 |
| 5,064,413 | 11/1991 | McKinnon et al. | 604/70 |
| 5,120,657 | 6/1992 | McCabe et al. | 435/287 |
| 5,149,655 | 9/1992 | McCabe et al. | 435/287 |
| 5,312,335 | 5/1994 | McKinnon et al. | 604/72 |
| 5,312,577 | 5/1994 | Peterson et al. | 264/154 |
| 5,383,851 | 1/1995 | McKinnon, Jr. et al. | 604/68 |
| 5,386,837 | 2/1995 | Sterzer | 128/898 |
| 5,399,163 | 3/1995 | Peterson et al. | 604/68 |
| 5,405,779 | 4/1995 | McCabe et al. | 435/287 |
| 5,421,816 | 6/1995 | Lipkovker | 604/20 |
| 5,466,220 | 11/1995 | Brenneman | 604/87 |
| 5,503,627 | 4/1996 | McKinnon et al. | 604/72 |
| 5,506,125 | 4/1996 | McCabe et al. | 435/172.1 |
| 5,520,639 | 5/1996 | Peterson et al. | 604/68 |
| 5,525,510 | 6/1996 | McCabe et al. | 435/285.3 |
| 5,584,807 | 12/1996 | McCabe | 604/71 |
| 5,599,302 | 2/1997 | Lilley et al. | 604/68 |
| 5,614,502 | 3/1997 | Flotte et al. | 514/34 |
| 5,630,796 | 5/1997 | Bellhouse et al. | 604/49 |
| 5,672,167 | 9/1997 | Athayde et al. | 604/892.1 |
| 5,700,245 | 12/1997 | Sancoff et al. | 604/145 |

FOREIGN PATENT DOCUMENTS

| | | | |
|---|---|---|---|
| 0370571 | 11/1989 | European Pat. Off. | A61M 5/30 |
| 9620022 | 7/1996 | WIPO | A61M 5/30 |
| 9624360 | 8/1996 | WIPO | A61K 31/705 |
| 9625190 | 8/1996 | WIPO | A61M 5/307 |

OTHER PUBLICATIONS

Powderject Pharmaceuticals PLC, company literature, 23 pages, undated.

"A piston–actuated shock–tube, with laser–Schlieren diagnostics", S.M.Hurst, et al., Rev. Sci. Instrum., vol. 64, No. 5, May 1993, pp. 1342–1346.

"Shock Waves in Chemistry and Physics", not dated, pp. 66–67 and 110–134.

*Primary Examiner*—John D. Yasko
*Assistant Examiner*—N. Kent Gring
*Attorney, Agent, or Firm*—Nutter, McClennen & Fish, LLP

[57] ABSTRACT

A drug delivery system includes a container having proximal and distal ends and a rapidly openable divider, replaceably disposed within the container to separate the container into a proximal chamber that is selectively gas impermeable and able to receive a pressurized gas and a distal chamber having an opening at a distal end thereof. A membrane is disposed between the opening in the distal chamber of the container and a biologic material, such as a patient's skin, treated with a medicament. In operation, rapid opening of the divider causes a shock wave to be generated and transmitted through the opening in the distal chamber to impinge on the membrane which transfers the shock wave to the biologic material. The system may further include a drug housing mountable in a fluid tight manner on the biologic material and an optional sealing element by which the fluid tight seal is created.

48 Claims, 9 Drawing Sheets

DRUG DELIVERY SYSTEM

BACKGROUND OF THE INVENTION

Various techniques are used to introduce medicinal drugs into a patient's body, including injection and oral administration of medicine in solid or liquid form. Injection is an effective way to rapidly introduce medicine into a patient's bloodstream. However, patients often experience anxiety and discomfort from injections. Further, infection due to needle contamination is of growing and significant concern.

One type of conventional "needleless" drug injection system includes a mechanism, such as a plunger, by which a narrow stream of medicine is forced out of a nozzle at a very high speed to penetrate the patient's skin. Illustrative "needleless" injection systems are described in U.S. Pat. Nos. 5,599,302 (Lilley et al.), 5,383,851 (McKinnon et al.) and 5,064,413 (McKinnon et al.). While such apparatus prevents infection due to needle contamination, injection of the high speed stream can still cause discomfort and anxiety.

While oral administration of medicine is often preferable to injection, this technique suffers certain drawbacks. For example, in some circumstances, manufacture of a drug in a form suitable for oral administration degrades the effectiveness of the drug. Other drawbacks are related to the taste of a liquid medicine, the shape and/or size of a pill or tablet form, and stomach irritation.

Another technique for administering certain medicines is by absorption through the patient's skin (i.e., transdermally). Conventional transdermal drug delivery techniques include the use of ultrasonic energy or other forms of high-frequency energy. For example, in U.S. Pat. No. 5.421,816 (Lipkovker), ultrasound energy is used to move a drug through a patient's skin into the bloodstream. In U.S. Pat. No. 5,386,837 (Sterzer), pulse shocks of high-frequency energy, such as RF, microwave, infra-red or laser energy, are employed to create transient pores in the membranes of targeted diseased cells through which drug or chemotherapeutic agents can easily enter the targeted cells. U.S. Pat. No. 5,614,502 (Flotte et al.) describes the use of high pressure impulse transients, as may be created by laser-induced ablation, in combination with the administration of certain compounds. The high pressure, laser generated impulse works in combination with the therapeutic compound by generally increasing cell permeability in the region of impulse administration.

As used herein, the term "drug delivery" refers to the action by which a drug, medicament, compound, chemical agent, biological agent or the like (collectively, "agents") passes from the outside of cell(s) to the interior of cell(s) to effect a therapeutic, chemical or biological activity. Drug delivery includes transdermal drug delivery, the passage of drugs, compounds and the like through tissue including organs and cell cultures, both in vivo and in vitro. The term "biologic material" encompasses skin, organ tissue, cell cultures and the like.

BRIEF SUMMARY OF THE INVENTION

The invention relates to a drug delivery system including a drug delivery initiator for generating a shock wave and a membrane receiving the shock wave and transmitting the shock wave to a target material. The target material may be a biologic material, such as a patient's skin, or a medicament in contact with a biologic material. The drug delivery initiator includes a first, proximal chamber that is selectively gas impermeable and is able to receive pressurized gas, a second, distal chamber having an opening at a distal end thereof and a rapidly openable divider mounted to separate the first and second chambers. The membrane is disposed adjacent to, or in contact with, the opening in the distal chamber of the initiator.

In operation, rapid opening of the divider causes a shock wave to be generated as pressurized gas is released from the proximal chamber into the distal chamber. The shock wave is transmitted through the distal opening of the initiator to impinge on the membrane which, in turn, transfers the shock wave to the biologic material. Impact of the shock wave on the skin increases the porosity of any of the biomembranes at or below the skin, thereby enhancing absorption of the medicament.

The medicament may be applied to the biologic material in various ways, including direct topical application or through a permeable or rupturable drug containing ampule that is positioned adjacent to the biologic material. In one embodiment, the medicament is topically applied with the use of a penetratable drug containing ampule or drug housing mountable in substantially fluid tight communication to the patient's skin. An optional sealing element provides the fluid tight communication between the drug housing and the patient's skin. To this end, the sealing element includes a cavity having an opening in the bottom surface and at least one piercing element. In use, the drug containing ampule is placed in the cavity of the sealing element and is punctured by the piercing element, causing the medicament to contact the patient's skin through the opening in the sealing element cavity. One embodiment of the sealing element includes straps with which the element is mountable over the patient's skin in the manner of a wrist watch.

The drug delivery initiator may be "closed-ended," with the membrane mounted to the distal chamber of the drug delivery initiator so as to cover the opening. Alternatively, the initiator may be "open-ended," with the membrane being a separate component or being mounted to, or integrally formed with the drug housing or mounted to, or integrally formed with the sealing element.

The rapidly openable divider disposed between the proximal and distal chambers of the drug delivery initiator may take various forms, such as a rupturable membrane, diaphragm or a valve. Such a rupturable diaphragm may be comprised of various materials. Exemplary metals from which the rupturable diaphragm can be made include, but are not limited to, titanium, titanium alloys, aluminum, tin, stainless steel and copper. Exemplary polymeric materials include, but are not limited to, polyaramid fibers, polyamides, cellulose, cellulose acetate, polyester, polyvinyl chloride and mylar. Further, the diaphragm may be self-rupturable, in response to a predetermined pressure differential across the diaphragm, or may be ruptured in response to an external force, such as an electric charge, heat or mechanical actuation.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Figure 1:
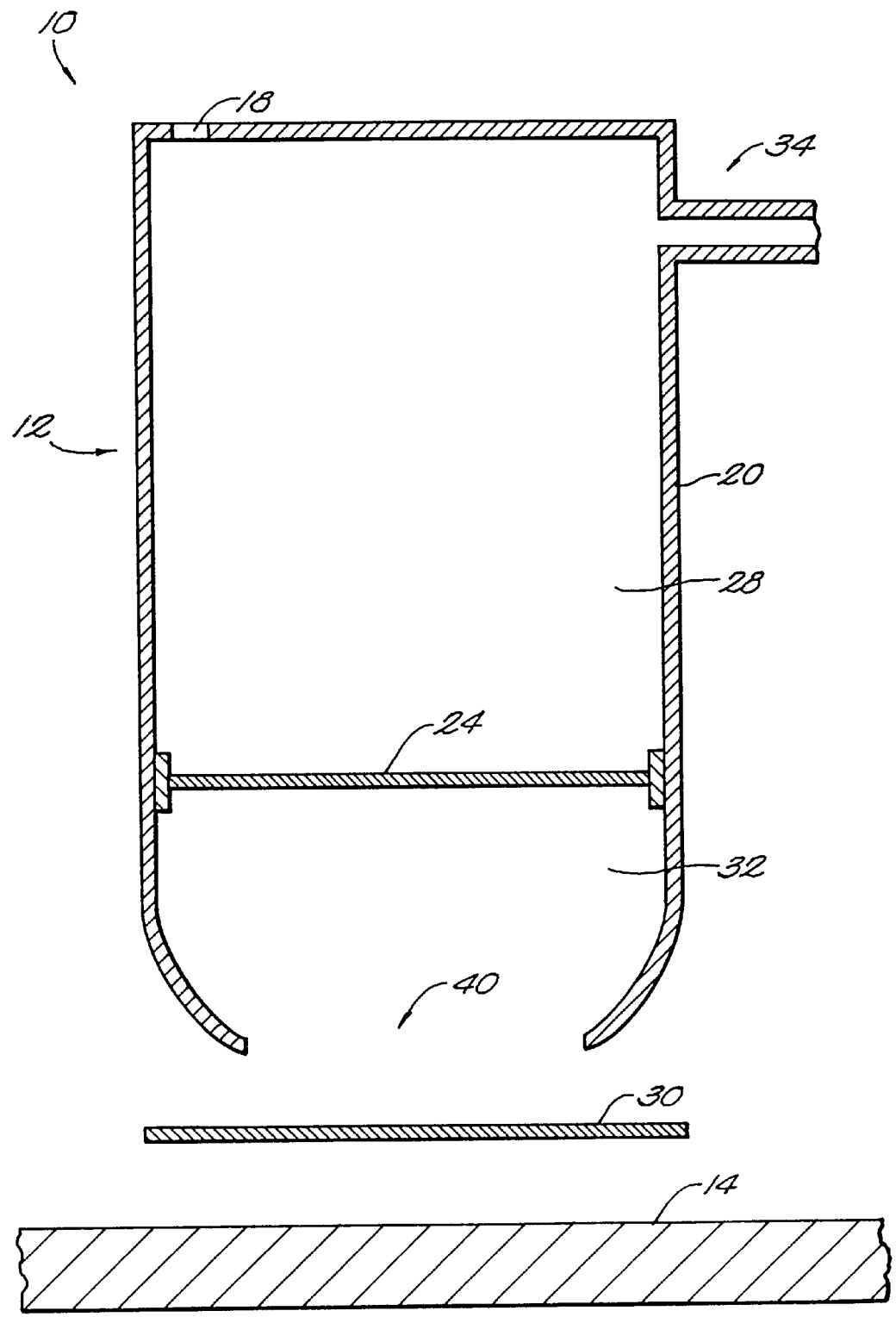
FIG. 1 is a cross-sectional view of a transdermal drug delivery system according to the invention.

Referring to FIG. 1, a shock wave generating system 10 suitable for drug delivery applications includes a shock wave initiator 12 and a shock wave transmission membrane 30. The initiator 12 includes a container 20 having a rapidly openable, or removable divider 24 positioned to separate the container into a first, proximal chamber 28 and a second, distal chamber 32. The proximal chamber 28 is selectively gas impermeable and is able to receive a pressurized gas from an external source (not shown) via a gas port 34. The container 20 communicates with the membrane 30 via an opening 40 at the distal end of the distal chamber 32.

In use, the distal opening 40 of the container 20 is brought into shock wave communication with the membrane 30 which is further brought into shock wave communication with a target material 14. The target material may be a biologic material, such as a patient's skin, or a medicament in contact with a biologic material. Rapid opening, or removal of the divider 24 causes a shock wave to be generated upon the release of pressurized gas from the proximal chamber 28 to the distal chamber 32. The shock wave travels through the distal opening 40 to impinge on the membrane 30 which transfers the shock wave to the biologic material 14.

The shock wave is a high-pressure wave propagating at supersonic speeds, with a typical rise time on the order of one to one-hundred nanoseconds and a useful duration on the order of several hundred nanoseconds, following which the shock wave dissipates significantly. Typical shock wave magnitudes are characterized by a pressure on the order of between one and five hundred bars.

The delivery apparatus and techniques described herein are suitable for transmitting shock waves to various biological materials to enhance absorption of various compounds, medicaments and other agents by the biologic material. For simplicity of illustration, the apparatus and techniques are described herein primarily with reference to transdermal drug delivery, with the biologic material 14 being a patient's skin. Other applications for the shock wave generating systems described herein include in vitro applications to effect absorption of such agents by cell cultures, and other in vivo applications, including gene therapy, invasive surgery and/or delivery of agents through forms of organs, tissue and physiological systems other than skin.

Impact of the shock wave on the biologic material (e.g., patient's skin) causes the porosity of the biologic material (i.e., the permeability of the cells) to increase temporarily, thereby enhancing absorption of the agent (i.e., diffusion of the agent through the cell wall). Typically, the shock wave propagates through the biologic material (e.g., patient's skin) to a depth on the order of a few centimeters before significant dispersion occurs.

The extent to which the cell porosity is increased can be manipulated by varying the rise time and magnitude of the generated shock waves. In general, the rise time and magnitude of the shock waves are selected to ensure that the permeability of the skin 14 is optimally affected, without destroying the viability of the target cells. As one example, the cell permeability is affected for a duration of between several seconds and several minutes and the temporary permeability increase is sufficient to permit a variety of medicinal compounds and other agents, with a wide range of molecular weights, to enter the cells. It is believed that the molecular weights of agents useful with the system of the invention ranges from about 100 kilodaltons to several thousand kilodaltons. It will be appreciated by those of ordinary skill in the art that various factors, other than the rise time and magnitude of the shock wave, affect the absorption of the medicament by the skin, including electrostatic forces between cell membranes, the form, type and amount of the compound and the pH level.

The patient's skin can be prepared for shock wave application by treatment with a medicament. The medicament may be administered either locally or systemically, by various conventional pharmaceutical techniques. For example, the medicament may be applied topically or internally (i.e., orally or with an injection, such as an intravenous, intramuscular or intradermal injection). Direct topical application may be performed prior to shock wave treatment, such as by spreading the compound over a localized region of the skin targeted for subsequent shock wave treatment. In some applications, it may be advantageous to wait a predetermined amount of time after application of the medicament and before shock wave application, in order to permit dispersion of the medicament. Alternatively, the compound may be present within a drug-containing ampule which is applied to the skin during and subjected to shock wave treatment, with the use of a drug housing, as described in conjunction with FIGS. 6–9. Application of shock waves to the skin following injection of an agent into the body renders the body more amenable to the effects of the agent.

The container 20 may take various forms, in terms of its size and shape. Ideally, the size of the container 20 has a height on the order of six to eight inches long, with a diameter on the order of one to two inches, with the height of the proximal chamber 28 being approximately four times greater than the height of the distal chamber 32. Generally, the container 20 is comprised of a material having suitable strength and gas impermeability characteristics. Exemplary materials for providing the container 34 include metals and metal alloys, such as stainless steel, copper and aluminum, and various polymeric materials.

In the illustrative embodiment, the container 20 is tapered so as to have a slightly smaller diameter at its distal end than at its proximal end and the opening 40 is substantially circular in shape. It will be appreciated by those of ordinary skill in the art that the particular size and shape of the container 20 and its features, including the distal opening 40, can be readily modified suit a particular application. As one example, the size of the distal opening 40 may be decreased in order to focus the shock waves transmitted therethrough.

Figure 5:
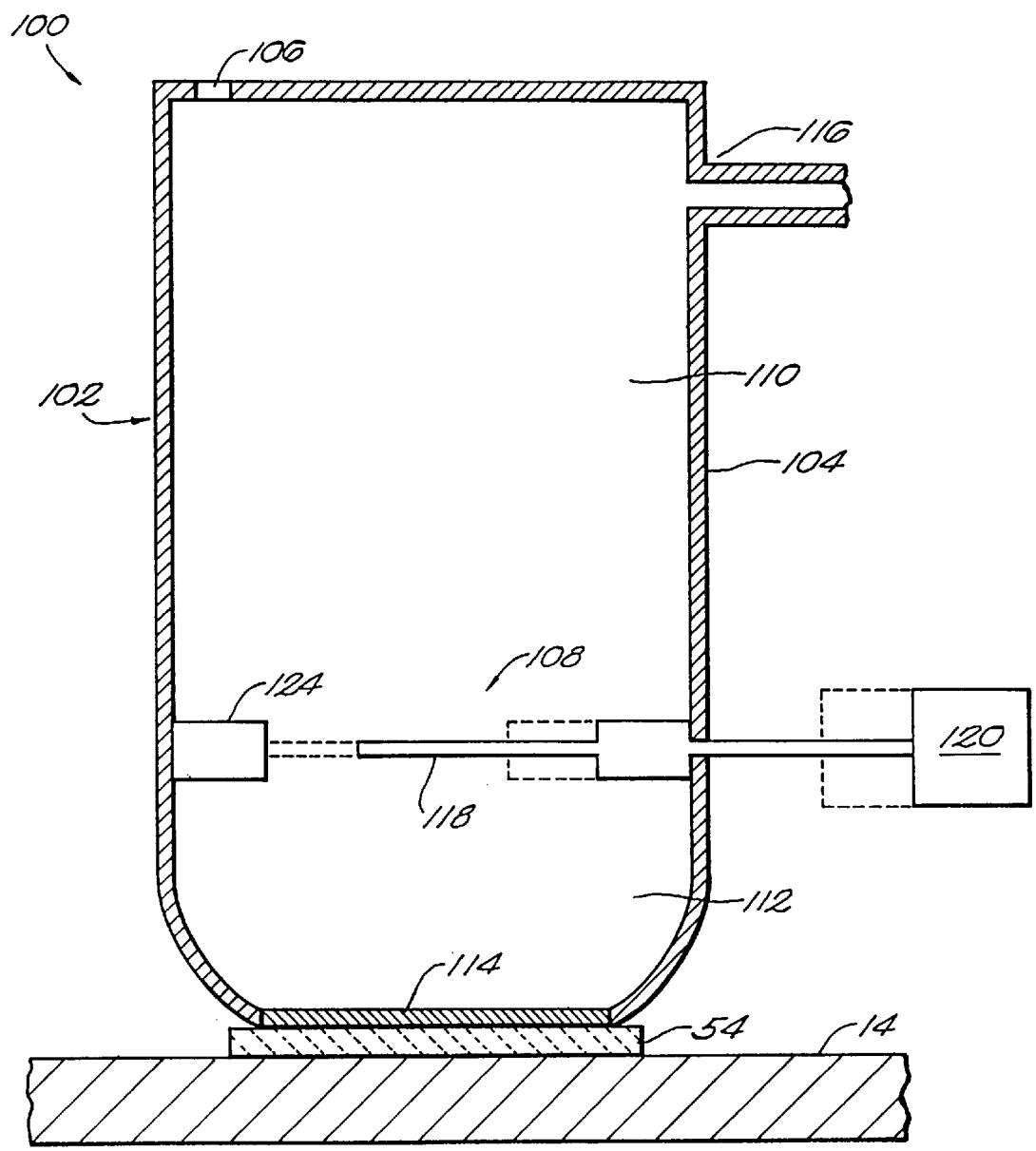
FIG. 5 is a cross-sectional view of a still further alternate transdermal drug delivery system according to the invention.

The rapidly openable divider 24 may take various forms, including a rupturable, gas impermeable diaphragm as shown in FIG. 1 or a valve as is shown in FIG. 5. In the case of a rupturable diaphragm providing the divider 24, the diaphragm is removably and replaceably mounted within the container 20, such as with the use of mounting brackets 46 fastened to, or integrally formed with the inner wall of the container 20.

Suitable materials for providing the gas impermeable diaphragm 24 include metals, such as titanium, titanium alloys, aluminum, tin, stainless steel and copper and polymeric materials, such as polyaramid fibers, polyamides, cellulose, cellulose acetate, polyvinyl chloride, polyester and mylar. The diaphragm 24 may be self-rupturable in response to the pressure differential across it exceeding a predetermined magnitude (i.e., the "rupture point"). Further, the gas impermeable diaphragm 24 may be scored and the rupture point may be varied by varying the scoring pattern and/or extent. Alternatively, the diaphragm 24 may be rupturable in response to an external force, such as an electric charge, heat or a mechanical action.

The shock wave transmission membrane 30 is deflectable in response to shock wave impact. However, the extent of deflection may be so small as to be undetectable by the naked eye and/or negligible. Suitable materials for fabricating the membrane 30 include metals, such as titanium, titanium alloys, aluminum, tin, stainless steel and copper and polymers, such as polyaramid fibers, polyamides, cellulose, cellulose acetate, polyvinyl chloride, polyester and mylar.

The membrane 30 may be gas impermeable or alternatively, may be gas permeable. A gas permeable membrane may include one or more perforations, preferably having a relatively small size as compared to the surface area of the membrane 30 and, more preferably, having a size on the order of 0.1 to 1.0 millimeters. The gas flowing through a gas permeable membrane works in conjunction with the force of the shock wave, albeit over a much longer time constant than the shock wave, to force the medicament into the patient's skin. While the shock wave lasts on the order of several hundred nanoseconds before dissipating significantly, the impact of gas from the distal chamber passing through the membrane 30 and to the medicament and patient's skin 14 continues for a duration on the order of milliseconds. Thus, once the shock wave has dissipated, the gas movement through the membrane 30 serves to provide additional force on the medicament and the patient's skin 14, thereby improving absorption of the medicament.

Figure 2:
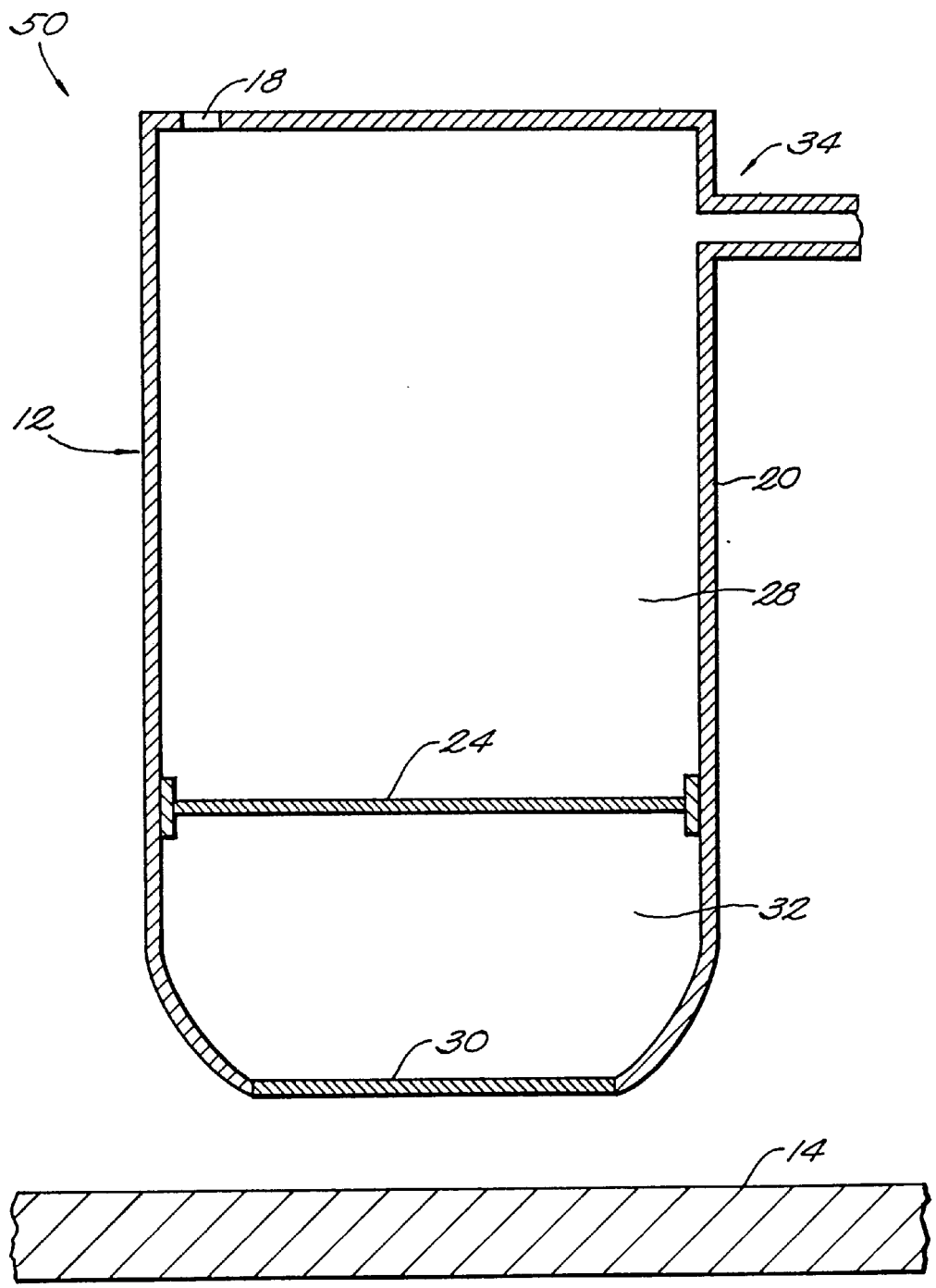
FIG. 2 is a cross-sectional view of an alternate transdermal drug delivery system according to the invention.
Figure 3:
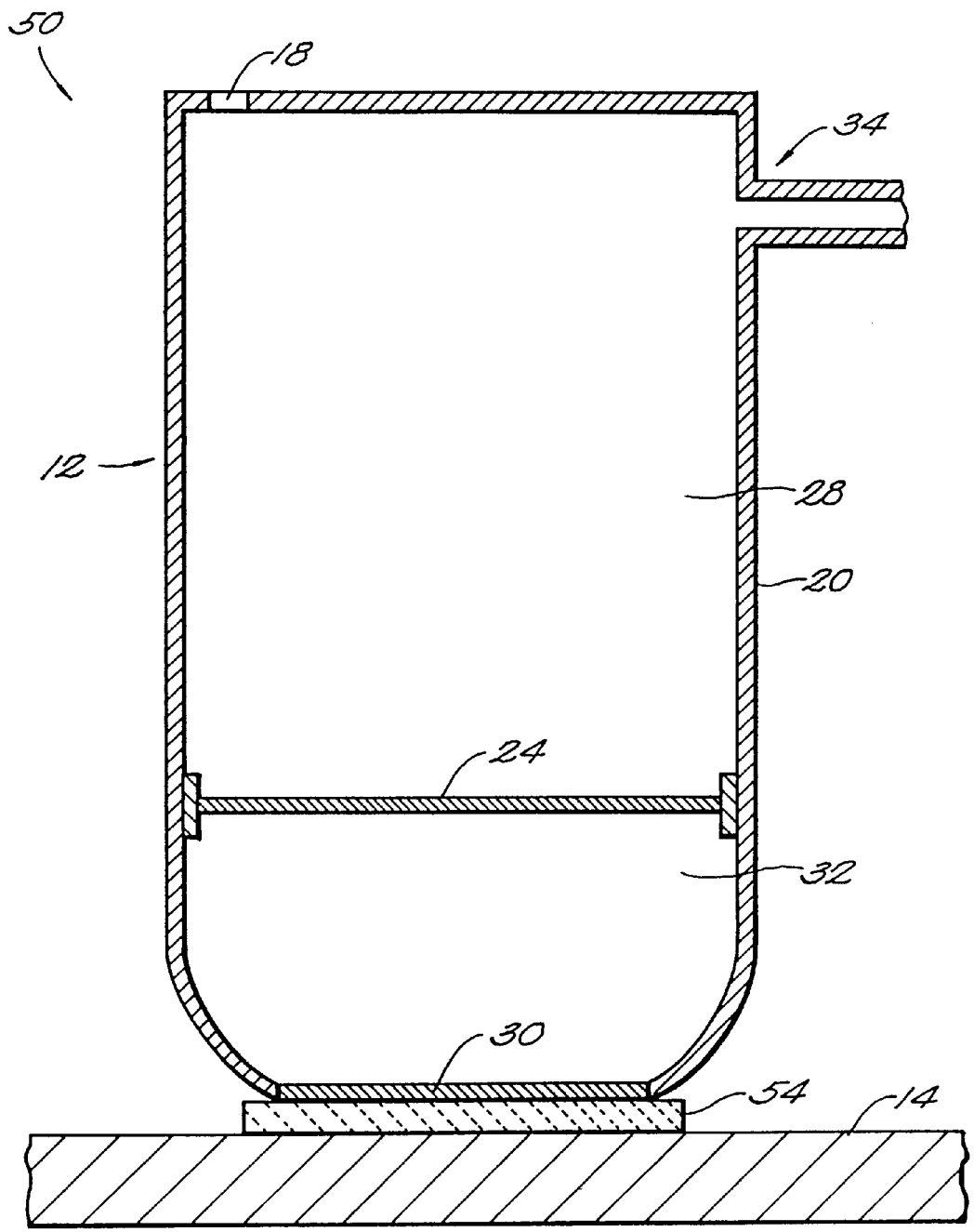
FIG. 3 is a cross-sectional view of the transdermal drug delivery system of FIG. 2 in use.
Figure 6:
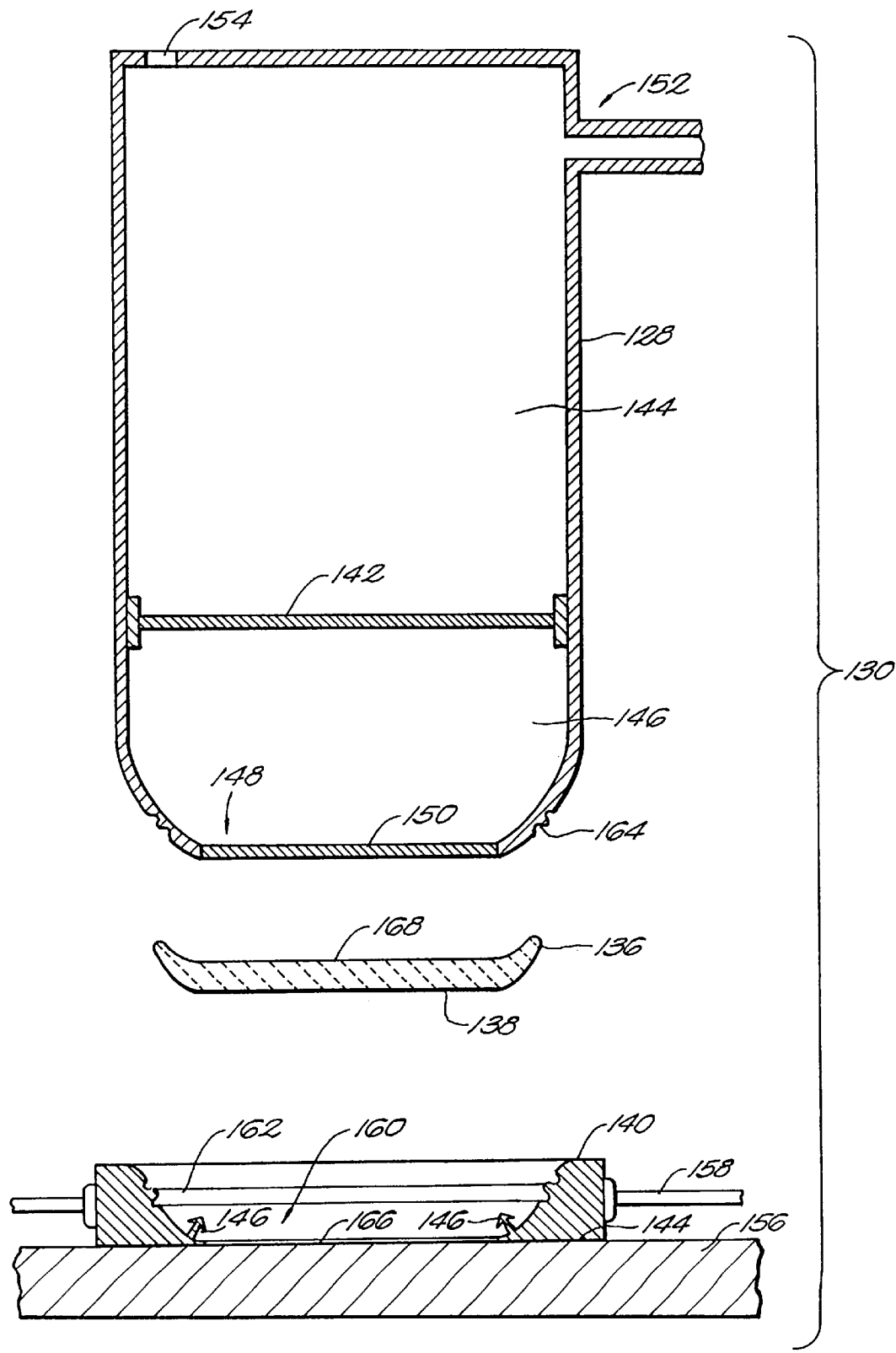
FIG. 6 an exploded, cross-sectional view of yet another alternate transdermal drug delivery system according to the invention.

The membrane 30 may be part of various components of the drug delivery system 10. For example, in the embodiment of FIG. 1, the membrane 30 is a separate component. Alternatively, the membrane may be mounted to the container 20 as shown in FIG. 2, may be part of an optional drug housing as shown in FIG. 3 or may be part of a sealing element as shown in FIG. 6.

In use, the distal chamber 32 of the container 20 is initially filled with a gas, at a predetermined pressure, and the proximal chamber 28 receives a pressurized gas via the gas port 34. In the illustrative embodiment, the distal chamber 32 is filled with air at ambient atmospheric pressure. Many pressurized gases are suitable for introduction into the proximal chamber 28, including carbon dioxide, hydrogen, argon, nitrogen, air and rare gases, including helium, argon, neon and xenon.

In the case where the divider 24 is a self-rupturable diaphragm, as gas is being pumped into the proximal chamber and when the pressure differential between the proximal and distal chambers 28, 32, respectively, reaches a predetermined magnitude, the diaphragm 24 ruptures. This rapid opening of the divider 24 causes a shock wave to be generated and transmitted into the distal chamber 32. The shock wave travels through the opening 40 at the distal end of the chamber 32 and impinges on the adjacent membrane 30 which, in turn, transmits the shock waves to the patient's medicament-treated skin 14. Impact of the shock waves on the patient's skin 14 causes the porosity of the skin cells to increase temporarily, as described above.

A release valve 18 in the wall of the proximal chamber 28 permits any gas remaining in the container 20 after shock wave generation to be purged. In this way, the proximal chamber 28 of the initiator container 20 is readied to accept pressurized gas for reuse.

With this arrangement, an effective drug delivery system is provided using an apparatus which is relatively simple and inexpensive. In this way, the advantages of transdermal drug delivery, as compared to injections and oral administration, are realized, without the drawbacks associated with complex and expensive equipment, such as ultrasonic and/or laser equipment.

The shock wave generating system 10 of FIG. 1 can be characterized as "open-ended" in the sense that the container 20 has an opening 40 at its distal end. FIG. 2 shows a "closed-ended" shock wave generating system 50 suitable for transdermal drug delivery, with like reference characters referring to like elements. In the embodiment of FIG. 2, the membrane 30 is mounted to the container 20, at the distal end of the distal chamber 32. More particularly, the membrane 30 is mounted to the container so as to cover the opening 40 at the distal end and, thus, to close the container, as shown, and may be mounted with a gas tight seal.

The system 50 includes container 20 in which the rapidly openable divider 24 is disposed to divide the container into the proximal chamber 28 and the distal chamber 32, as described above in conjunction with FIG. 1. The gas port 34 permits introduction of a pressurized gas into the distal chamber 28 from an external gas source (not shown).

Referring to FIG. 3, use of the closed-ended shock wave generating system 50 is illustrated, with the container 20 brought into shock wave communication with the patient's skin 14 for generation and transmission of shock waves to the patient's skin 14 upon the rapid opening of the divider 24. More particularly, in the illustrated application, the container 20 is brought into contact with a medicament, or drug 54 suitable for absorption by the skin 14.

The medicament 54 may be provided in various forms in accordance with the various manners by which the skin is treated. As examples, the medicament 54 may be a liquid, gel, ointment or creme which is applied topically to the patient's skin 14. Alternatively, the medicament 54 may be contained in a penetratable drug housing, as in the embodiments of FIGS. 6–9, or a drug housing which is permeable to the drug.

Figure 4:
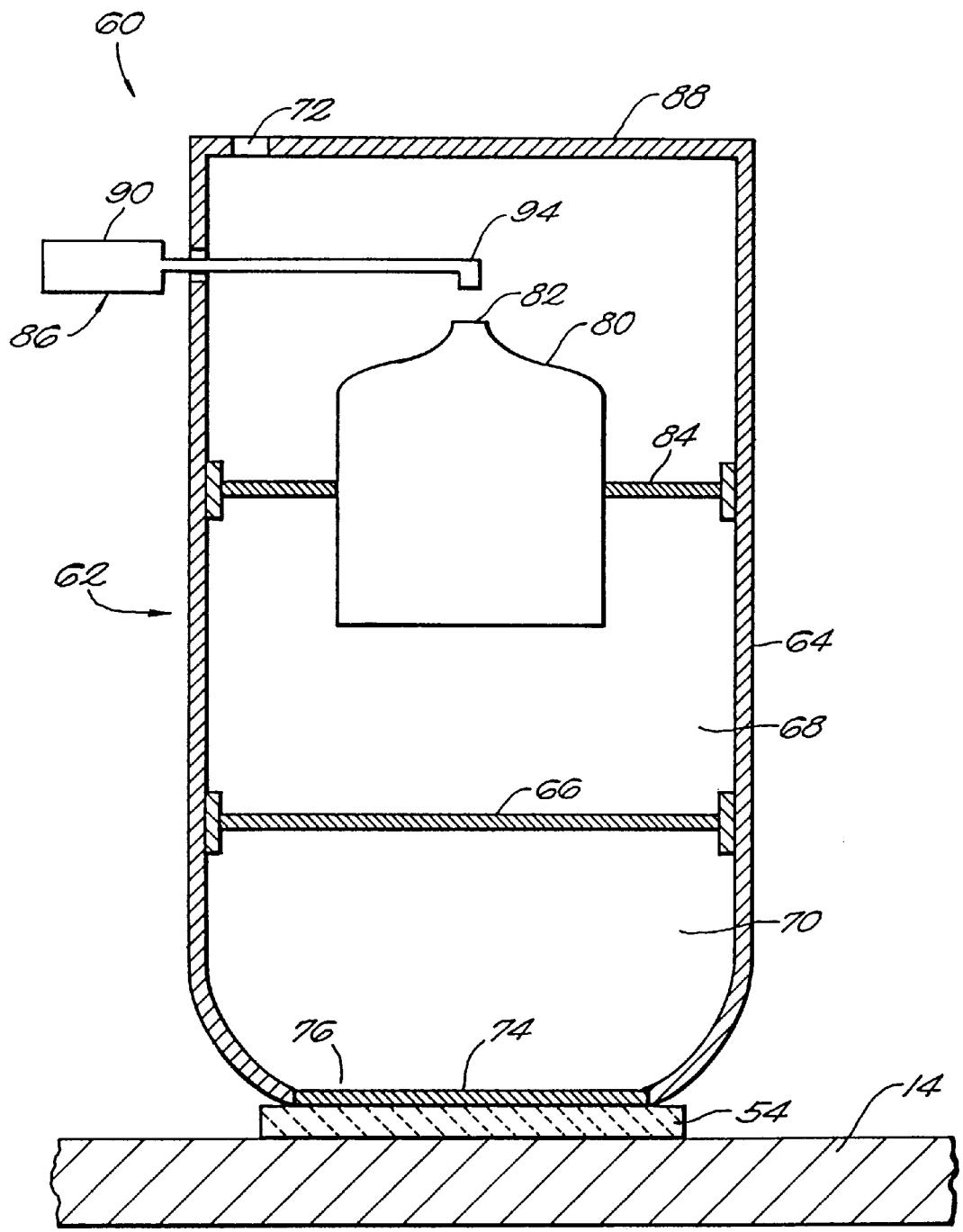
FIG. 4 is a cross-sectional view of a further alternate transdermal drug delivery system according to the invention.

Referring to FIG. 4, a shock wave generating system 60 includes an alternative mechanism for introducing pressurized gas into the proximal chamber. The shock wave generating system 60, like the above-described embodiments, includes an initiator 62 comprising a container 64 in which a rapidly openable divider 66 is disposed to separate the container 64 into a first, proximal chamber 68 and a second, distal chamber 70 having an opening at the distal end. The system 60 of FIG. 4 is closed-ended in the sense that the shock wave transmission membrane 74 is mounted to the container 64 at the distal end so as to cover the distal opening 76 and is operative in the same manner as described above to generate and transfer shock waves through the membrane 74 to the medicament 54 and patient's skin 14.

A pressurized gas cartridge 80 is removably and replaceably disposed in the proximal chamber 68. In order to facilitate removal and replacement of the cartridge 80 for subsequent use of the shock wave generating system 60, the container 64 is provided with a removable cover 88 which is designed to maintain the gas impermeability of the container 64, such as with the use of a rubber gasket. A release valve 72 is disposed through the cover 88 in order to permit any gas remaining in the container 64 after use to be purged.

A mounting bracket, or frame 84 is provided for securing the cartridge 80 within the proximal chamber 68. It will be appreciated by those of ordinary skill in the art, however, that various techniques are suitable for mounting the cartridge 80 within the proximal chamber 68. An actuator 86 accessible from the exterior of the container 64 permits the pressurized gas cartridge 80 to be punctured upon actuation, thereby releasing the pressurized gas into the proximal chamber 68. Release of the pressurized gas into the proximal chamber 68 causes the pressure differential across the diaphragm 66 to exceed its "rupture point." The rupturing of the diaphragm 66 causes shock waves to be generated and transmitted through the distal chamber 70 and membrane 74 in the manner described above.

The actuator 86 may take various forms. In the illustrative embodiment, the actuator 86 is a lever having a handle 90 and a puncturing element 94. In use, moving the handle 90 toward the proximal end of the container 64 causes the puncturing element 94 to move into contact with, and puncture the mouth 82 of the cartridge 80. It will be appreciated by those of ordinary skill of the art that various mechanical mechanisms, other than the illustrated puncturing element 94, are suitable for puncturing the pressurized gas cartridge 80. Further, the cartridge 80 may be punctured by other means.

Referring to FIG. 5, a closed-ended shock wave generating system 100 including an initiator 102 for transmitting shock waves to a patient's skin 14 includes a rapidly openable divider 108 in the form of a valve. The valve 108 is disposed in a container 104 of the initiator 102 so as to divide the container 104 into a first, proximal chamber 110 and a second, distal chamber 112 having a membrane 114 mounted over an opening at the distal end. A gas port 116 permits pressurized gas to be introduced into the proximal chamber 110 from an external source (not shown) and a release valve 106 permits gas remaining in the container 104 after use to be purged, thereby readying the system 100 for subsequent use.

The valve 108 includes a sliding portion 118 which is movable by an actuator 120 between a first, closed position (shown by dotted lines) in which the sliding portion 118 abuts a stop 124 and a second, open position (shown by solid lines) in which the sliding portion 118 is spaced from the stop 124. With the sliding portion 118 of the valve in the closed position, the valve provides a gas impermeable seal between the proximal chamber 110 and the distal chamber 112.

Actuation of the valve 108 via actuator 120 causes very rapid movement of the sliding portion 118 from the first, closed position to the second, open position. It is this rapid opening of the valve which causes a shock wave to be generated and transmitted through the distal chamber 112 to impact the shock wave transmission membrane 114, medicament 54 and skin 14 in the manner described above.

The actuator 120 may take various forms, such as an electric circuit, a mechanical actuator, or an electromechanical actuator. Further, it will be appreciated by those of ordinary skill in the art that while the illustrated valve 108 is relatively simple in design, more elaborate valves, such as gate valves or piston-based valves may be used.

Referring to FIG. 6, an alternate transdermal drug delivery system 130 includes a closed-ended shock wave initiator 134 of the type described above in conjunction with FIG. 2, a drug housing 136 and a sealing element 140. The drug housing 136 is adapted for containing a medicament and includes a first surface 138 adapted for being penetrated to permit the medicament to flow towards the patient's skin 156 and a second, opposite surface 168.

The shock wave initiator 134 includes a container 128 in which a rapidly openable divider 142 in the form of a rupturable diaphragm is mounted so as to divide the container into a first, proximal chamber 144 and a second, distal chamber 146 having an opening 148 at the distal end thereof. A shock wave transmission membrane 150 is mounted to the container 128 so as to cover the opening 148 at the distal end of the chamber 146. A gas port 152 permits a pressurized gas to be introduced into the first chamber 144 from an external source (not shown) and a release valve 154 permits gas remaining in the container 128 after use to be purged.

The sealing element 140 is mountable to the patient's skin 156 and is adapted for receiving the drug housing 136 and providing a fluid tight seal between the drug housing 136 and the patient's skin 156. To this end, the sealing element 140 includes a cavity 160 sized and shaped to receive the drug housing 136 and having an opening 166 in the bottom surface 144 for permitting the medicament to contact the patient's skin 156. The sealing element 140 further includes a mechanism for mating with the container 128. In the illustrative embodiment, screw threads 162 disposed in the sealing element cavity 160 are mateable with complimentary screw threads 164 disposed around the distal end of the container 128. It will be appreciated by those of ordinary skill in the art that various mechanisms may be used for mating the sealing element 140 and the container 128, such as a Luer lock.

The sealing element 140 includes a mechanism for penetrating the surface 138 of the drug housing 136, thereby causing the medicament to flow through the opening 166 toward the patient's skin 156. In the illustrative embodiment, piercing elements 146 project upward from the cavity 160 of the sealing element so as to puncture the surface 138 of the drug housing.

In the illustrative embodiment, the sealing element 140 includes a straps 158 which permit the element to be worn by the patient in the manner of a wrist watch. It will be appreciated by those of ordinary skill in the art however that the sealing element 140 may take various forms.

Figure 8:
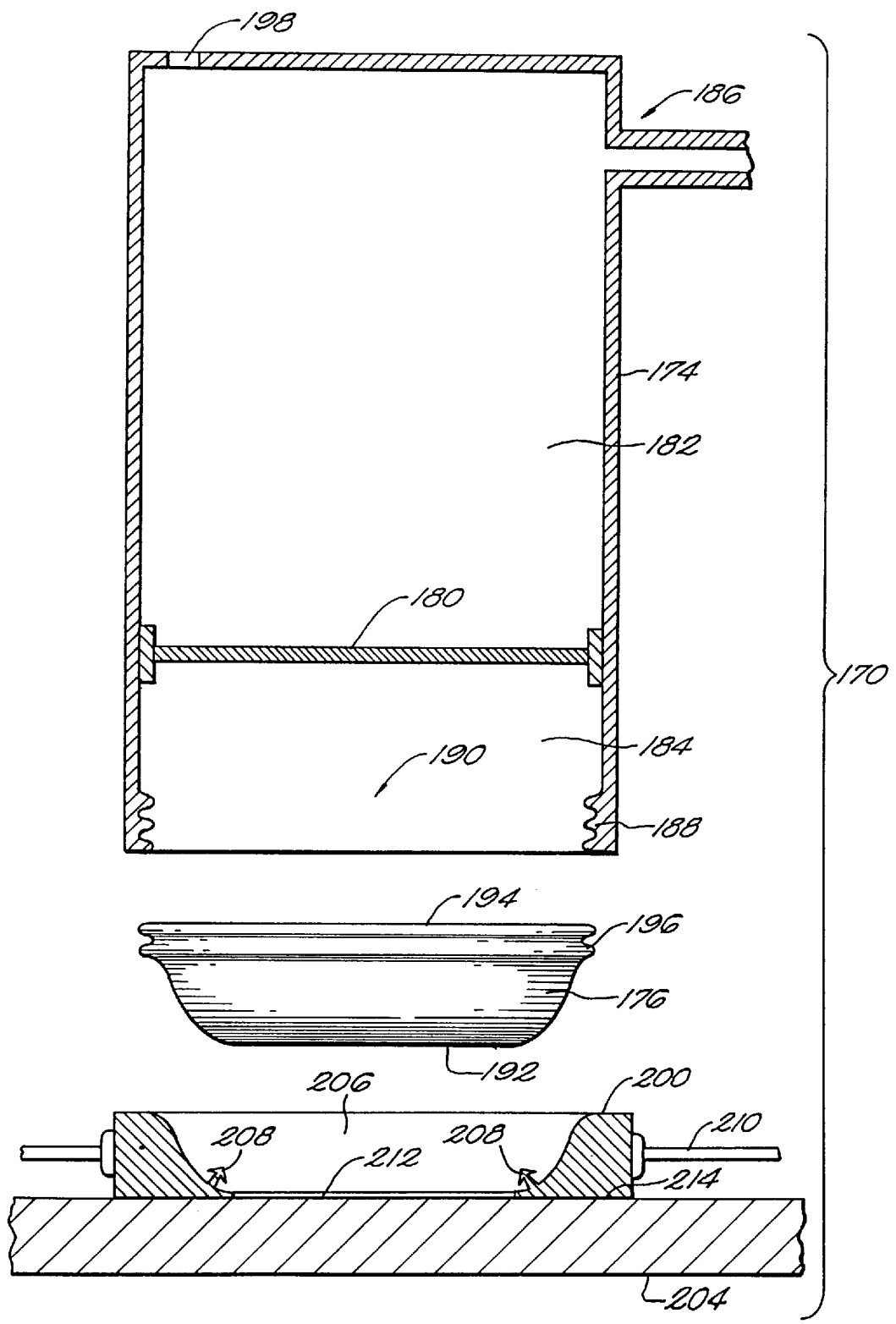
FIG. 8 is an exploded, cross-sectional view of still another transdermal drug delivery system according to the invention.

The drug housing 136 may be comprised of various materials and the size and shape of the housing 136 may be readily varied to suit a particular application and sealing element 140, as will become apparent. For example, the drug housing may be adapted to mate with the drug delivery initiator container 128 as shown in FIG. 8. As another example, the drug housing 136 may not require puncturing, but rather may be permeable to the medicament or may be ruptured by impact of the shock waves.

Figure 7:
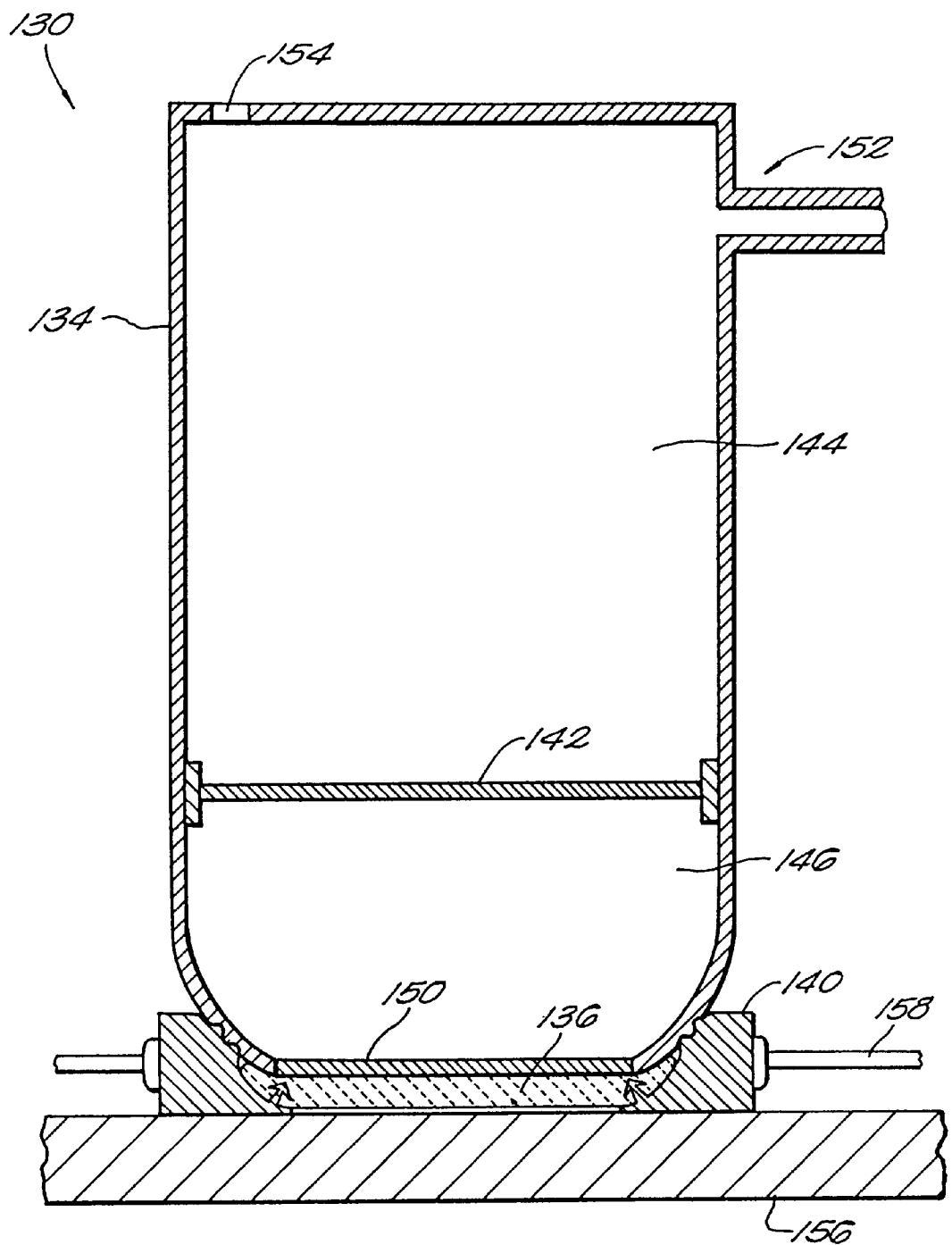
FIG. 7 is a cross-sectional view of the transdermal drug delivery system of FIG. 6 in use.

Referring also to FIG. 7, the transdermal drug delivery system 130 is shown in assembly, prior to shock wave generation. The drug housing 136 is disposed within the cavity 160 of the sealing element 140 and the bottom surface 138 of the drug housing has been penetrated by piercing elements 146. The shock wave initiator container 128 is brought into shock wave communication with the drug housing 136 and the patient's skin 156 by mating the distal end of the container chamber 146 with the mateable portion 162 of the sealing element 140. More particularly, the container 128 is placed over the sealing element 140 and is screwed down so that the screw threads 164 of the initiator container 128 engaged the screw threads 162 of the sealing element 140. With the system 130 disposed as shown in FIG. 7, a pressurized gas is introduced into the first chamber 144 via the gas port 152 for rupturing the diaphragm 142 as described above in order to generate a shock wave for transmission to the patient's skin 156.

A further alternate transdermal drug delivery system 170 is shown in FIG. 8, with like numerals referring to like elements. In the system 170, the drug delivery container 174 is mateable to a drug housing 176 and the shock wave transmission membrane is provided as part of the drug housing 176. More particularly, the initiator container 174 is open-ended and includes a rapidly openable divider 180 mounted to divide the initiator container 174 into a proximal chamber 182 and a distal chamber 184, as shown. A gas port 186 permits communication of an external source (not shown) of pressurized gas with the proximal chamber 182 and a release valve 198 permits gas remaining in the container 174 after use to be purged. The distal chamber 184 terminates at a mating portion 188 which defines an opening 190 at the distal end. In the illustrative embodiment, the mating portion 188 includes screw threads.

The drug housing 176 is adapted for containing a medicament and has a first surface 192 adapted for being punctured or otherwise opened to release the medicament and a second, opposite surface 194. The drug housing 176 further includes a mating portion 196 suitable for mating to portion 188 of the initiator container 174. The second surface 194 of the drug housing 176 provides the shock wave transmission membrane (like membrane 150 in FIG. 6, for example). This membrane 194 may be integrally formed with the drug housing 176 or, alternatively, may be a separate component positioned over the surface of the drug housing 176.

A sealing element 200 is provided for receiving the drug housing 176 and for affecting a fluid tight seal between the drug housing and the patient's skin 204. The sealing element 200 is substantially similar to sealing element 140 (FIGS. 6 and 7), with the exception that the sealing element 200 does not include mating portion 162. This is because the initiator container 174 mates with the drug housing 176 as opposed to mating with the sealing element 200. The sealing element 200 thus includes a cavity 206 which is adapted for receiving the drug housing 176 and in which piercing elements 208 are disposed for piercing the first surface 192 of the drug housing. An opening 212 in the bottom surface 214 of the sealing element permits the medicament to flow toward the patient's skin. The illustrative sealing element 200, like sealing element 140, includes straps 210 to permit the sealing element to be worn by the patient in the manner of a wrist watch.

Figure 9:
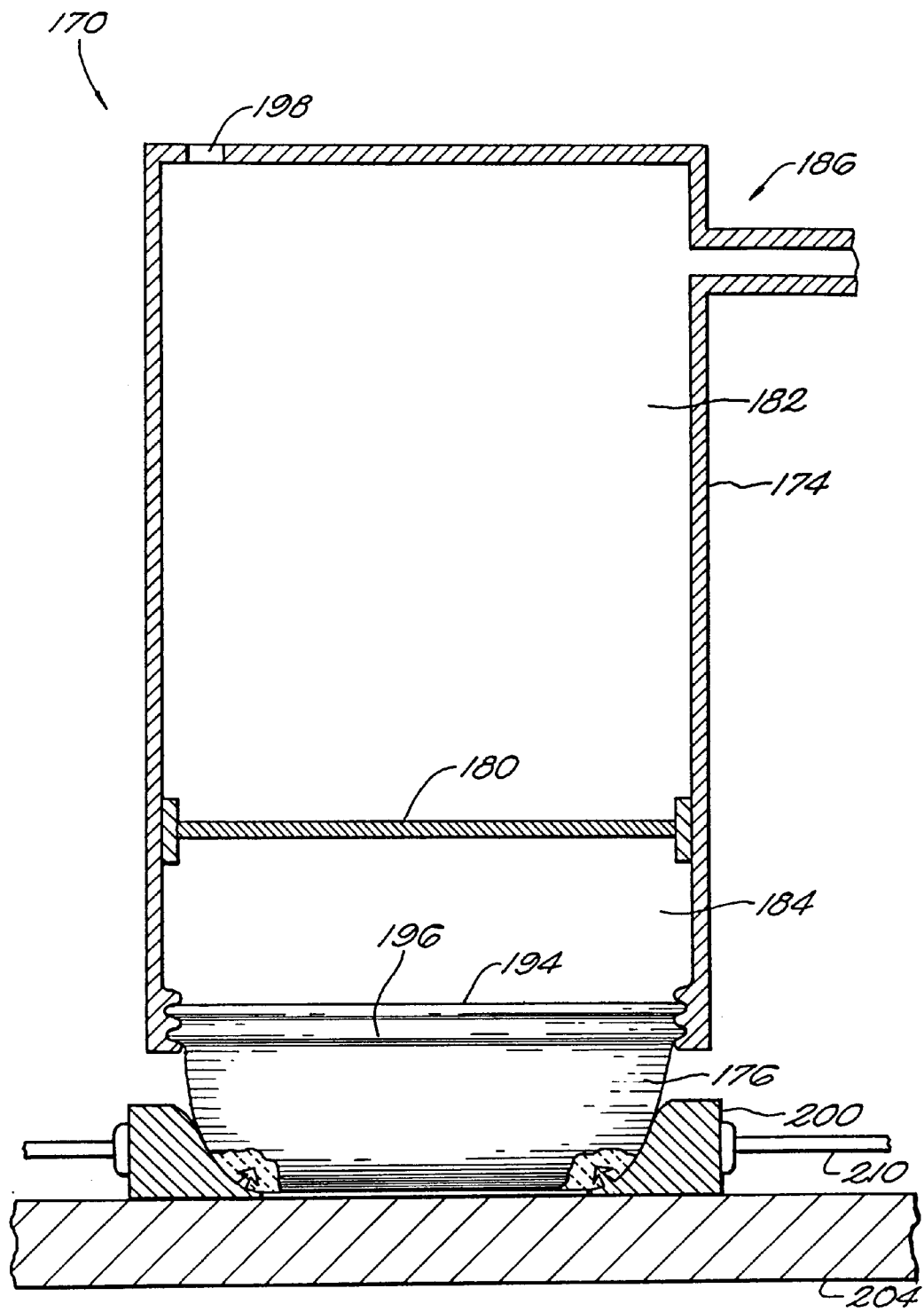
FIG. 9 is a cross-sectional view of the transdermal drug delivery system of FIG. 8 in use.

Referring to FIG. 9, the transdermal drug delivery system 170 is shown placed over the patient's skin 204 and ready for use. The drug housing 176 is positioned within the cavity 206 of the sealing element 200, with the first surface 192 of the drug housing penetrated by the piercing elements 208. Thus, the medicament contacts the patient's skin 204 via the opening 212 within the sealing element 200. The drug delivery initiator container 174 is brought into engagement with the drug housing 176, with the threaded portion 188 of the container mated with the threaded portion 196 of the drug housing. With the system 170 thus positioned, the container 174 is ready to receive a pressurized gas via the gas port 186. Rapid rupture of the diaphragm 180 due to a predetermined pressure differential between the proximal chamber 182 and the distal chamber 184 causes a shock wave to be created and transmitted through the distal chamber 184, distal opening 190 and drug housing 176 to impinge on the patient's skin 204.

One of ordinary skill in the art will appreciate that the container 20 may be altered in size and shape to be useful in applications other than transdermal drug delivery. As examples, the distal chamber 31 may be comprised of a flexible material and/or system can be dimensioned to be used with or in a catheter to be useful in minimally invasive surgical techniques (e.g., endoscopic surgery) or open surgery.

Having described the preferred embodiments of the invention, it will now become apparent to one of ordinary skill in the art that other embodiments incorporating their concepts may be used. For example, it will be appreciated by those of ordinary skill in the art that various phenomena, in addition to shock waves, may be utilized to increase the porosity of a biologic material so as to enhance medicament absorption, such as electrical discharge, laser ablation, piezoelectric devices and ultrasound. It is felt therefore that these embodiments should not be limited to disclosed embodiments but rather should be limited only by the spirit and scope of the appended claims. All publications and references cited herein are expressly incorporated herein by reference in their entirety.

What is claimed is:

1. A drug delivery system, comprising:
   a drug housing having a medicament receiving chamber with a first, open end mountable in fluid tight communication with a biologic material and a second end; and
   a drug delivery initiator including:
      a first, proximal chamber that is selectively gas impermeable, said first chamber being configured to receive pressurized gas;
      a second, distal chamber having an opening at a distal end thereof adjacent to the second end of the drug housing; and
      a rapidly openable divider disposed between the first and second chambers, and effective upon opening to propagate a shock wave through said distal chamber to said second end of the drug housing.

2. The system of claim 1 wherein the second end of the drug housing is open.

3. The system of claim 1 further comprising a membrane disposed between the distal end of the second chamber of the drug delivery initiator and the second end of the drug housing.

4. The system of claim 3 wherein the membrane is mounted to the drug housing.

5. The system of claim 3 wherein the membrane is integrally formed with the drug housing.

6. The system of claim 3 wherein the membrane is made from a metal selected from the group consisting of titanium, titanium alloys, aluminum, tin, stainless steel and copper.

7. The system of claim 3 wherein the membrane is made from a polymer selected from the group consisting of polyaramid fibers, polyamides, cellulose, cellulose acetate, polyvinyl chloride, polyester and mylar.

8. The system of claim 3 wherein the membrane is gas impermeable.

9. The system of claim 3 wherein the membrane includes one or more gas permeable perforations.

10. The system of claim 9 wherein the gas permeable perforations are relatively small in size as compared to the surface area of the membrane.

11. The system of claim 1 further comprising a sealing element effective to create the fluid tight communication between the biologic material and the first end of the drug housing.

12. The system of claim 11 further comprising a membrane mounted to the sealing element.

13. The system of claim 1, comprising a valve selected from the group consisting of mechanically actuated valves, electrically actuated valves and gas actuated valves.

14. The system of claim 1 wherein the rapidly openable divider is a rupturable, gas impermeable diaphragm.

15. The system of claim 14 wherein the diaphragm is replaceably mounted within the drug delivery initiator.

16. The system of claim 15 wherein the target material is a medicament in contact with a biologic material.

17. The system of claim 14 wherein the diaphragm is self-rupturable in response to a pressure differential exceeding a predetermined magnitude.

18. The system of claim 14 wherein the diaphragm is scored.

19. The system of claim 14 wherein the diaphragm is rupturable in response to an external force selected from the group consisting of electric charges, heat and mechanical actuation.

20. The system of claim 14 wherein the diaphragm is made from a metal selected from the group consisting of titanium, titanium alloys, aluminum, tin, stainless steel and copper.

21. The system of claim 14 wherein the diaphragm is made from a polymeric material selected from the group consisting of polyaramid fibers, polyamides, cellulose, cellulose acetate, polyvinyl chloride, polyester and mylar.

22. The system of claim 1 wherein the pressurized gas is communicated to the first chamber of the drug delivery initiator through a gas port formed in the first chamber, from an external gas source.

23. The system of claim 1 wherein the medicament is selected from the group consisting of a gel or liquid.

24. The system of claim 1 wherein the first chamber is adapted to receive a pressurized gas selected from the group consisting of carbon dioxide, hydrogen, argon, nitrogen, air and rare gases, including helium, argon, neon and xenon.

25. A shock wave generating system, comprising:

a container having proximal and distal ends; and a rapidly openable divider replaceably disposed within the container to separate the container into a proximal chamber that is selectively gas impermeable and configured to receive a pressurized gas, and a distal chamber having an opening at a distal end thereof for placement at a target material, said divider being effective to generate a shock wave when rapidly opened such that the shock wave is transmitted through the distal chamber to the target material.

26. The system of claim 25 wherein the target material is a biologic material.

27. The system of claim 26 wherein the biologic material is a patient's skin.

28. The system of claim 25 further comprising a membrane having a first surface that receives the shock wave generated upon rapid opening of the divider and the release of pressurized gas from the first chamber to the second chamber, and a second, opposed surface that transmits the shock wave received by the first surface.

29. The system of claim 28 wherein the membrane is gas impermeable.

30. The system of claim 28 wherein the membrane is gas permeable.

31. The system of claim 30 wherein the membrane includes one or more gas permeable perforations.

32. A drug delivery system, comprising:
a container;

a rapidly openable divider disposed within the container so as to divide the container into a first, proximal chamber that is selectively gas impermeable and is configured to receive a pressurized gas, and a distal chamber having an opening at a distal end thereof through which a shock wave is transmitted upon rapid opening of the divider; and a gas permeable membrane having a first surface that receives the shock wave and a second, opposed surface that transmits the shock wave received by the first surface to a target material.

33. The system of claim 32 wherein the target material is a biologic material.

34. The system of claim 32 wherein the target material is a medicament in contact with a biologic material.

35. The system of claim 32 wherein the membrane includes one or more gas permeable perforations.

36. The system of claim 35 wherein the gas permeable perforations are relatively small in size as compared to the surface area of the membrane.

37. The system of claim 32 wherein the gas permeable membrane is provided by a drug housing mounted in fluid tight communication with the target material.

38. The system of claim 32 further comprising a sealing element effective to create a fluid tight communication between the target material and a drug housing, wherein the gas permeable membrane is mounted to the sealing element.

39. A method of administering a drug, comprising the steps of:
providing a drug to a biologic material;

providing a container having a rapidly openable divider disposed therein so as to divide the container into a first, proximal chamber that is selectively gas impermeable and is configured to receive a pressurized gas, and a distal chamber having an opening at a distal end thereof; and rapidly opening the divider so as to release pressurized gas from the first chamber and create a shock wave which propagates through the second chamber and the opening of the distal end of the second chamber to the biologic material whereby the drug enters the biological material.

40. The method of claim 39 wherein the container providing step includes providing the rapidly openable divider with a gas impermeable diaphragm.

41. The method of claim 40 wherein the divider opening step includes opening the divider in response to a predetermined pressure differential between the first and second chambers.

42. The method of claim 40 wherein the divider opening step comprises the step of opening the divider in response to an external force selected from the group consisting of electric charges, heat and mechanical actuation.

43. The method of claim 39 further comprising the step of preparing the biologic material by applying a drug to the biologic material.

44. The method of claim 39 further comprising the step of providing a membrane adjacent to the opening of the distal end of the distal chamber of the container through which the shock wave is transmitted from the second chamber to the biologic material.

45. The method of claim 44 wherein the membrane providing step includes permitting gas to flow through the membrane to the target material.

46. The method of claim 39 wherein the drug providing step includes topically applying the drug to the biologic material.

47. The method of claim 39 wherein the drug providing step includes injecting the drug into a patient to which the drug is being administered.

48. The method of claim 47 wherein the drug is injected in a manner selected from the group consisting of intravenously, intradermally and intramuscularly.

* * * * *